(12) United States Patent
Dang et al.

(10) Patent No.: US 10,994,050 B2
(45) Date of Patent: May 4, 2021

(54) HIGH YIELD AND HIGH PRECISION BONE GRAFT SUBSTITUTE FROM STEM CELLS

(71) Applicant: The Regents of the University of California, Oakland, CA (US)

(72) Inventors: Alan Dang, San Francisco, CA (US); Bernard Halloran, Pacifica, CA (US)

(73) Assignee: The Regents of the University of California, Oakland, CA (US)

(*) Notice: Subject to any disclaimer, the term of this patent is extended or adjusted under 35 U.S.C. 154(b) by 97 days.

(21) Appl. No.: 15/774,279

(22) PCT Filed: Nov. 8, 2016

(86) PCT No.: PCT/US2016/061003
§ 371 (c)(1),
(2) Date: May 7, 2018

(87) PCT Pub. No.: WO2017/083312
PCT Pub. Date: May 18, 2017

(65) Prior Publication Data
US 2018/0326117 A1 Nov. 15, 2018

Related U.S. Application Data

(60) Provisional application No. 62/252,957, filed on Nov. 9, 2015.

(51) Int. Cl.
*A61F 2/28* (2006.01)
*A61L 27/26* (2006.01)
(Continued)

(52) U.S. Cl.
CPC .............. *A61L 27/26* (2013.01); *A61F 2/28* (2013.01); *A61F 2/2846* (2013.01); *A61L 27/18* (2013.01);
(Continued)

(58) Field of Classification Search
CPC .. A61L 27/3821; A61L 27/56; A61L 27/3608; A61L 27/26; A61F 2/28;
(Continued)

(56) References Cited

U.S. PATENT DOCUMENTS 8,535,388 B2   9/2013   Ganey
8,734,831 B2   5/2014   Kim et al.
(Continued)

OTHER PUBLICATIONS

Leotot et al., Bone-Forming Capacity and Biodistribution of Bone Marrow-Derived Stromal Cells Directly Loaded Into Scaffolds: A Novel and Easy Approach for Clinical Applications of Bone Regeneration, Oct. 28, 2014; Cell Transplantation, vol. 24, pp. 1945-1955 (Year: 2014).*
(Continued)

*Primary Examiner* — Brian A Dukert

(57) ABSTRACT

The invention comprises various materials and methods for the formation of bone within a patient using implanted bodies that are seeded with bone forming cells. The implants of the invention may comprise interlocking building blocks which allow for the formation of any desired structure. The geometry of the resulting bone structure can be tailored with great precision, and can be controllably integrated with native bone as desired. Advantageously, the methods result in the formation of functional, structured bone and avoid overgrowth, undergrowth, and the use of growth factors such as BMP-2.

1 Claim, 3 Drawing Sheets

(51) Int. Cl.
  *A61L 27/24* (2006.01)
  *A61L 27/56* (2006.01)
  *A61L 27/18* (2006.01)
  *A61L 27/32* (2006.01)
  *A61L 27/36* (2006.01)
  *A61L 27/38* (2006.01)
  *A61L 27/54* (2006.01)

(52) U.S. Cl.
  CPC ............... *A61L 27/24* (2013.01); *A61L 27/32* (2013.01); *A61L 27/3608* (2013.01); *A61L 27/3637* (2013.01); *A61L 27/3821* (2013.01); *A61L 27/56* (2013.01); *A61L 27/54* (2013.01)

(58) Field of Classification Search
  CPC ............ A61F 2/4455; A61F 2002/2835; A61F 2002/30622
  See application file for complete search history.

(56) References Cited

U.S. PATENT DOCUMENTS

| | | | |
|---|---|---|---|
| 8,758,791 B2 | 6/2014 | McKay | |
| 8,920,511 B2* | 12/2014 | Southard | A61F 2/30744 623/23.51 |
| 2007/0191963 A1* | 8/2007 | Winterbottom | A61L 27/58 623/23.5 |
| 2007/0224678 A1* | 9/2007 | McGowan | A61L 27/10 435/402 |
| 2012/0003185 A1* | 1/2012 | Meretzki | A61L 27/3843 424/93.3 |

OTHER PUBLICATIONS

Choi et al., Effect of Ascorbic Acid on Bone Marrow-Derived Mesenchymal Stem Cell Proliferation and Differentiation, 2008; Journal of Bioscience and Bioengineering, vol. 105, pp. 586-594 (Year: 2008).*

Marycz, K. et al., Application of bone marrow and adipose-derived mesenchymal stem cells for testing the biocompatibility of metal-based biomaterials functionalized with ascorbic acid, Biomedical Materials, 2013, vol. 8, doi: 10.1088/1748-6041/8/6/065004, pp. 1-12. See abstract; 2. Materials and methods on p. 2; 3. Result on pp. 4-7.

Choi, K. et al., Effect of ascorbic acid on bone marrow-derived mesenchymal stem cell proliferation and differentiation, Journal of Bioscience and Bioengineering, 2008, vol. 105, pp. 586-594. See the whole document.

* cited by examiner

HIGH YIELD AND HIGH PRECISION BONE GRAFT SUBSTITUTE FROM STEM CELLS

CROSS-REFERENCE TO RELATED APPLICATIONS

This application claims priority to International Application No. PCT/US2016/061003, entitled "High Yield and High Precision Bone Graft Substitute from Stem Cells," filed on Nov. 8, 2016, which claims priority to U.S. Provisional Application No. 62/252,957, entitled "High Yield and High Precision Bone Graft Substitute from Stem Cells," filed on Nov. 9, 2015, each of which is incorporated by reference herein in its entirety.

BACKGROUND OF THE INVENTION

Autologous bone grafting is used in the treatment of a variety of orthopedic conditions. However, the harvesting of bone for the graft, typically from the iliac crest, causes various morbidities, including pain, infection, and weakened bone, and lengthens the duration of surgery and recovery. Accordingly, it would be advantageous to have a bone forming material that substitutes for conventional graft material, avoiding the extraction of bone from the patient for transplant.

Various bone graft substitutes have been developed. For example, the Medtronic INFUSE™ system comprises a collagen sponge containing bone morphogenetic protein (BMP). When the sponge is implanted, native cells migrate into the matrix and form bone structures. Research groups have also investigated the use of transplanted osteoblasts cultured within collagen matrices.

The prior art methodologies suffer from various drawbacks. Prior art methods often do not efficiently remodel structured bone. Second, the inclusion of BMP or other growth factors (e.g. human growth hormone and VEGF) with cultured cells may increase inflammation and may increase the risk of cancer forming in the transplanted cells or surrounding tissues. Also, BMP-treated cells tend to overgrow to form chaotic disordered structures, while transplanted osteoblasts without BMP treatment fail to grow adequate bone mass.

Accordingly, there remains a need in the art for novel bone forming materials: that are easily produced; that robustly form bone structures yet do not overgrow; that do not rely on exogenous growth factors; and which result in the formation of ordered bone. Disclosed herein are novel compositions and novel and improved methodologies for the formation of bone tissue, which provides the robust formation of structured bone tissue and which enables the creation of replacement bone structures with unprecedented precision.

SUMMARY OF THE INVENTION

The scope of the invention encompasses various aspects. In one aspect, the invention encompasses novel methods of creating bone structures with precise geometries. In another aspect, the invention encompasses an improvement to the prior art cell culture methods which are used to create bone structures. In another aspect, the invention encompasses novel compositions of matter which can be transplanted into subjects to create new bone structures. In another aspect, the invention encompasses methods of creating new bone structures from existing bone tissues. In another aspect, the invention encompasses novel bone graft procedures which are enabled by the greatly improved bone substitutes described herein. The scope of the invention further comprises methods of making and loading the implant bodies with cells, as described herein. In one embodiment, the invention comprises making a medicament comprising an implant body. In another embodiment, the invention comprises making a medicament comprising an implant body loaded with cells.

Importantly, the novel methods and associated compositions of the invention can be used to create precisely shaped bone structures that are continuous with native bone. The bone structures created using the inventions described herein comprise functional, structured bone, with no heterotopic overgrowth. The novel inventions herein also avoid the problematic use of BMP-2 or other growth factors. Additionally, the use of building block implants contemplated herein allows for a myriad of diverse structures to be made using a standard set of implants.

DETAILED DESCRIPTION OF THE INVENTION

Figure 1A:
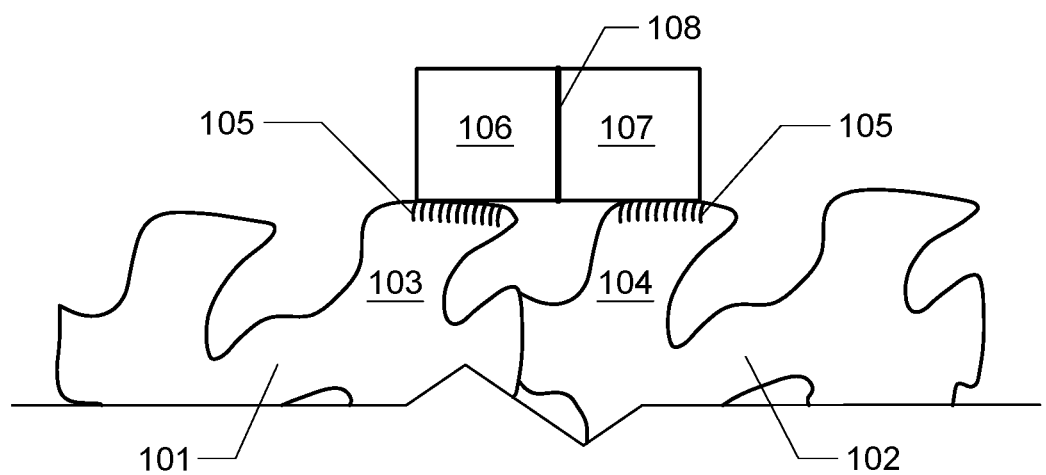
FIG. 1a depicts an exemplary implementation of the invention in performing a lumbar fusion. To join two vertebrae (101 and 102), a continuous formation of two implant bodies comprising cubic blocks (106 and 107) is formed across two transverse processes (103 and 104). The blocks are placed upon scored or decorticated regions (105) of the native bone. The blocks contact each other at one face (108), optionally by means of interlocking structures.
Figure 1B:
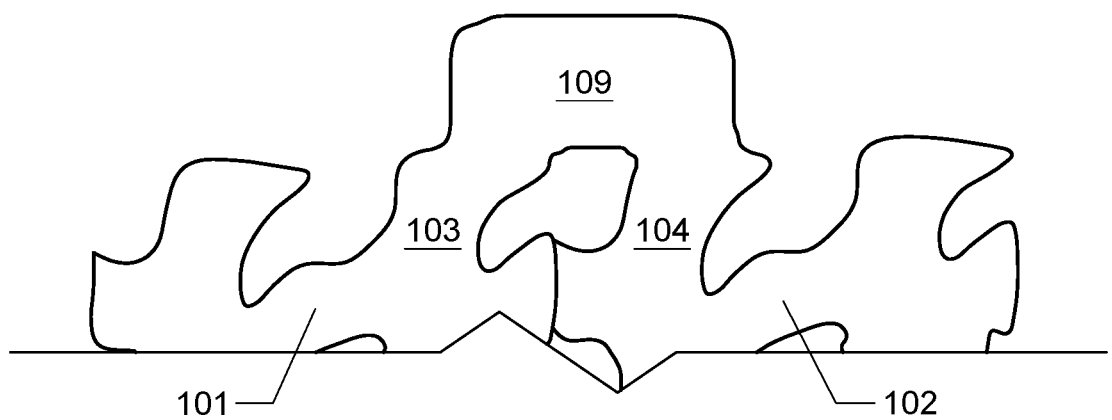
FIG. 1b depicts the lumbar fusuion several weeks later. The implant bodies have formed a new bone structure (1090 that is continuous with the native bone at the previously scored or decorticated regions, bridging the two transverse processes 103 and 104.

The inventions described herein are based upon various discoveries regarding the behavior of cultured and transplanted cells and the development of novel methodologies based thereon. The objective of the several inventions is to create bone structures within the body in a highly controlled manner, for example, to repair, replace, and augment bones that have been damaged, degenerated, or otherwise compromised.

For convenience, the methods of the invention will be described herein as being directed to a "patient," referring to a human patient in need of bone replacement or repair treatment or bony augmentation. However, it will be understood that the scope of the invention encompasses all animal species, including veterinary subjects and test animals.

In one aspect, the scope of the invention can be described as a process comprising the following steps: isolation of bone marrow stromal cells (BMSC's); expansion of BMSC's; differentiation of BMSC's into bone precursor cells; loading of BMSC's and bone precursor cells into implant bodies; the implantation of one or more implant bodies into the patient; and the formation of bone structure by the implanted one or more implant bodies. It will be understood that the overall process described herein is novel, and that individual steps and methods within the overall protocol also represent novel processes, and improvements to known methodologies, for generating bone from transplanted cells. The scope of the invention further encompasses novel compositions of matter described and employed in the methodologies disclosed herein, e.g. implant bodies and bony structures formed thereby. The scope of the invention further encompasses methods of making a medicament comprising the implantable structures described herein. Each element of the overall process will be described in detail below.

It will be understood that the processes and compositions of the invention may be employed in any number of applications, including bone graft procedures such as the repair of fractures, bone defects, nonunions, infections, and osteonecrosis. Furthermore, the inventions herein may be utilized to create fusions, for example, lumbar fusions. For example, a the fusion may comprise a lumbar fusion across transverse processes or between the vertebral bodies in the intervertebral disc space region or interbody space.

Isolation of BMSC's and Differentiation into Osteoblast Precursors. One aspect of the invention is the use of bone precursor cells to create bone structures. A primary step in certain of processes of the invention is obtaining bone marrow stromal cells (BMSC's). In one embodiment, the source of the BMSC's is bone marrow. In another embodiment, the source of BMSC's is morselized bone chips. In alternative embodiments, BMSC's are derived from pluripotent stem cells or multipotent mesenchymal cells from any source, including adipose tissue, peripheral blood, placental tissue, or other known sources. Autologous cell sources or cells from donors, e.g. immune matched donors, may be utilized.

The inventors of the present disclosure have advantageously discovered an age effect on the efficacy of transplanted cells. In general, mesenchymal cells recovered from older individuals perform better than cells derived from younger individuals in terms of structural organization and qualitative quality of bone formed. This is particularly advantageous for clinical applications such as a spine surgery where patients are generally older. In mice, for example, optimal marrow donors are aged 6 to 36 months. In humans, cells may be recovered from individuals of any age, with optimal marrow donors being individuals of greater than 40 years of age, for example over 60 years of age.

In one embodiment, the source of the BMSC's is bone marrow. The marrow may be suspended in an appropriate growth medium that will support the maintenance of marrow cells. For example, in one embodiment the growth medium comprises DMEM:F12 (in a 1:1 ratio), supplemented with serum (for example FBS) or xeno-free serum substitutes, and optionally supplemented with antibiotics. The marrow can be gently agitated to create a cell suspension. Thereafter, the suspension can be plated in plastic culture dishes or other culture surfaces.

Preferably, the density of cells in the cell suspension is determined prior to plating, so that cell plating density can be controlled. The inventors of the present disclosure have advantageously discovered that the cell plating density of the isolated marrow cells is critical in the formation of healthy osteoblasts. A plating density of between 125,000 to 375,000 cells per $cm^2$ should be used, with optimal results attained at about 255,000 cells per $cm^2$. In the heterogeneous mix of cells, approximately 1/400,000 cells represents fully multipotent BMSCs in the population, however other osteoblast precursors and associated cells are present. Optimal cell density may be attained using standard cell counting and dilution methods known in the art.

Following cell plating, the bone marrow cells are expanded. The cells are incubated at or near 37° C. The plated cells are then grown for a period of time to allow sufficient expansion of cells. The growth medium is preferably refreshed, for example, being changed approximately every other day. BMSC's are adherent to plastic culture dishes and wells and will form expanding patches of cells. Growth periods may be any sufficient to expand the plated BMSC's, for example, growth periods of 48-96 hours. A 70-75 hour growth/propagation phase, i.e. about 3 days, produces the best results in BMSCs harvested from mice.

After cell growth the propagating BMSC's are differentiated or partially differentiated towards a bone fate. Differentiation may be promoted by the use of a differentiation medium comprising a basal medium supplemented with agents that will promote the differentiation of the BMSC's to osteoblasts. For example, the propagation medium may comprise the primary medium used during the propagation phase, further supplemented with: β-glycerophosphate, for example at a concentration of 2-4 mM, e.g. 3 mM; and ascorbic acid, for example at a concentration of 25-100 µg/mL, for example at 50 µg/mL. In the case of human cells, dexamethasone should also be included in the differentiation medium, for example at a concentration of about 0.1 µM.

Culture in the differentiation medium should take place for a period of time until abundant differentiated cells are visible. Colonies of differentiated cells will form, with densely packed colonies expanding over the culture surface. For example, the cells may be differentiated for about 5-9 days (8-12 days after initial plating), with optimal results attained after about 7 days in the differentiation medium. The medium should be refreshed with new differentiation medium every 2-3 days. Cultures should remain at or near 37° C.

At this stage, the cell cultures will constitute a mixed culture of bone precursor cells, including residual BMSC's, osteoblast precursors, and other cells that have the potential to contribute to, regulate, or stimulate bone formation, in various stages of differentiation. These bone precursor cells are harvested for addition to the implant body. The cells may be harvested by adding trypsin to the culture vessel, for example 0.05% trypsin in EDTA, or using a like protease capable of dissociating adherent cells from culture vessel surfaces. After incubation in the dissociation agent, the cells can be mechanically scraped from the culture vessel surface and resuspended in fresh differentiation medium. The density of viable cells in the suspension may be determined by analyzing an aliquot of the suspension in a hemocytometer or like device. Trypan blue or like viability stain may be used to differentiate living from dead cells.

Implant bodies. The next stage in the process of the invention is to load the bone precursor cells into the implant body. An implant body, as used herein, refers to an object which will hold bone precursor cells and which can be implanted within the body of the patient, and which will form a bone structure that conforms to the same shape as the implant body. The key properties of the implant body are its ability to hold and support the growth and differentiation of bone precursor cells and its dimensions (shape and size).

With regards to composition, the entirety or majority of the implant body will comprises a transplant matrix material or scaffold, which is a porous, bio-compatible material capable of absorbing cell solutions and binding, adsorbing, absorbing, adhering, or otherwise holding cells within the matrix. In a preferred implementation, the matrix material comprises a material comprising chemical moieties that will bind, adsorb, or otherwise hold ascorbic acid. Generally, the transplant matrix material will be resorbable, however it can alternatively be a persistent material that remains integrated with the bone formed from it.

Exemplary transplant matrix materials include reconstituted Type 1 collagen sponges. Transplant matrix materials may comprise porcine skin sponge material, such as GELFOAM™ (Pfizer) or OSTEOFIL™ or DBM™ (Medtronic)). Transplant matrix materials may comprise bovine sponge material, for example, such as HELISTAT™ and DURAGEN™ (Integra) and PROGENIX™ (Medtronic)). Transplant matrix materials may comprise β-tricalcium phosphate material, for example, such as CHRONOS™ (DePuy/Johnson and Johnson). Transplant matrix materials may comprise microfibrillar collagen sponges, for example, such as AVITENE™ (Bard)). Transplant matrix materials may comprise ceramic/collagen composite scaffolds, for example, such as MOZAIK™ (Integra), FORMAGRAPH™ (NuVasive), MASTERGRAFT™ Matrix/Putty/Strip, (Medtronic), VITOSS™ (Stryker), or COPIOS™ (Zimmer). Other exemplary matrix materials include polymeric materials including polyurethane scaffolds synthesized from lysine-di-isocyanate, for example that has been copolymerized with ascorbic acid and glycerol or polyethylene glycol. Another exemplary matrix material is a plant based matrix, for example comprising cellulose, hemicellulose, and/or lignin. For example, plant based matrices may be derived from rattan or bamboo, such as those produced by GREENBONE ORTHO™. Transplant matrix material may also comprise admixtures of the aforementioned materials.

In a preferred implementation, the matrix component of the implant body will be functionalized with ascorbic acid. Advantageously, the presence of ascorbic acid in the transplant matrix will promote BMSC's and bone precursor cells to differentiate into osteoblasts and other mature bone cells. The directed differentiation promoted by ascorbic acid advantageously results in the formation of robust, structured bone. The effective concentration of ascorbic acid within the transplant matrix material can range from 50 mcg/mL to 500 mcg/mL.

Ascorbic acid functionalization of the matrix can be accomplished in various ways. In one implementation, ascorbic acid is admixed with the matrix material at the time the implant body is formed. In another implementation, the matrix material is infused with a solution of ascorbic acid prior to seeding with cells. In a preferred implementation, the infusion is performed just prior to loading the implant body with cell solution. For example, the matrix material may be infused with a solution of ascorbic acid ranging from 25-200 µg/ml ascorbic acid, for example in the range of 50-100 µg/ml. For example, porcine sponge material may be infused with a solution of about 50 µg/ml ascorbic acid. For example, β-tricalcium phosphate material may be infused with a solution of about 100 µg/ml ascorbic acid. The infusion step may comprise an incubation of the implant body in a solution of ascorbic acid. For example, the incubation period may vary from 15-75 minutes, for example, from 15-60 minutes, e.g. for about 30 minutes. The incubation is preferably performed at or near physiological temperatures, i.e. at or near 37° C. The incubation period advantageously enables the ascorbic acid to bind, adhere, adsorb, or otherwise associate with the matrix material such that it is more persistent. After the incubation period is complete, a substantial portion of the liquid medium present in the implant body should be removed, to restore the absorbent properties of the matrix so that it may effectively receive and retain cell solution. Medium can be withdrawn by placing the implant body on an absorbent surface, for example sterile filter paper.

In one implementation, the matrix material is admixed with materials comprising slow-release ascorbic acid formulations. Such materials will, under physiological conditions, release ascorbic acid for an extended period of time. Exemplary slow-release materials include ascorbic acid present in a carrier such as a polymeric material or hydrogel. Exemplary carriers include polylactic acid, polyglactin, caprolactone polymers, hyrdrox-ypropyl methylcellulose, polyethylene oxide materials, poly(2-hydroxyethyl methacrylate, hyaluronic acid, and other materials known in the art. Such materials may be present in the form of nanoparticles, microspheres, or other bodies, for example being infused into the matrix materials or being admixed with the matrix material at the time the implant body is formed.

The ascorbic acid that is used to functionalize the matrix may comprise any form of ascorbic acid. In a preferred implementation, unoxidized ascorbic acid is used, as inventors of the present invention have determined that this form is a more potent promoter of osteoformation. It will also be understood that any ascorbic acid analog, variant, or mimic which recapitulates the biological activity of ascorbic acid may be used instead.

The implant body may further comprise structural components to lend strength, flexibility, shaping, or other properties to the implanted bone substitute. In one embodiment, the structural materials will have physical properties (e.g. stiffness, compressibility, etc.) matched to the native bone which the implant body is intended to replace or augment. Exemplary structural materials include, polymeric, ceramic, biologic, metal or composite structures. Examples of a such materials include acrylonitrile butadiene styrene (ABS), polylactic acid (PLA), polyether ether ketone (PEEK), carbon fiber reinforced polymers, calcium phosphates, bioglass, chromic gut, titanium, and stainless steel. The structures may encase, be encased within, or be interspersed with the transplant matrix material. The structural materials may comprise, for example fibers, ribs, beams, mesh, or other structures. In one implementation, the structural materials are resorbable, gradually disappearing as the implant body develops into a bone structure. In an alternative implementation, the structural materials are persistent and reinforce the bone formed by the implant body.

A key component of the implant body will be its physical dimensions, i.e. its shape and size. Advantageously, the implant bodies of the invention may comprise any shape or size. The implant body may be manufactured using any appropriate process known in the art, for example, being molded, pressed, cut, or milled, for example with the aid of computerized CNC milling equipment, to the desired shape and size. The implant body may also be formed through any number of additive manufacturing techniques including printing, robocasting, extrusion, photopolymerization, binder jetting, or sintering.

In one implementation the implant body is formed in a custom shape and size which is congruent with a specific section of bone to be replaced or formed within a patient. For example, in one embodiment, the target region for the implant within the patient is mapped by a three-dimensional scanning modality and the scan is used to specify and define the shape of the implant body. For example, a missing section of bone or a damaged section of bone to be replaced in the patient may be mapped by high resolution three dimensional X-ray or micro-CT, and the resulting data can then be used to guide the manufacturing of a custom implant body precisely conforming to the mapped target. This method allows for the formation of precisely tailored implants that conform to the irregular shapes found in damaged bones.

In another embodiment, the implant body is a mass produced object having a standard shape approximating that of a specific bony structure to be replaced in the patient, for example a structure such as the patella, interevertebral disc, vertebral body, auditory ossicle. Additional structures may comprise long bones (e.g. tibia, femur, ulna, radius), clavicles, ribs, and phalanges (bones of the hands and feet). Such "off-the-shelf" implants can be produced in a range of sizes, conforming to various patient body sizes, such as those of children, adolescents, adult females and adult males.

In another embodiment, the implant bodies of the invention are produced as discreet building blocks, which can be used to build the implant body into any desired structure. Building blocks having planar surfaces that can be readily abutted next to one another are preferred. For example, implant bodies may comprise cubes, cuboids, prisms, spheres, cylinders, flanged-beams (e.g. I- and H-beams), and other common shapes. For example, in one embodiment, implant bodies comprise cubes, for example cubes of 3 mm per side, may be used. The implant bodies may comprise channels or grooves to increase surface area and/or facilitate the exposure of the cells held within to blood and nutrients in the patient. In one embodiment, the invention comprises a kit of two or more implants comprising polyominos, which are polyforms made up of cubic subunits. The kit may comprise dominos, trominos, tetrominos, etc., wherein the plurality of forms can be interlocked in various configurations to create larger objects with diverse 3-dimensional geometries.

Figure 2:
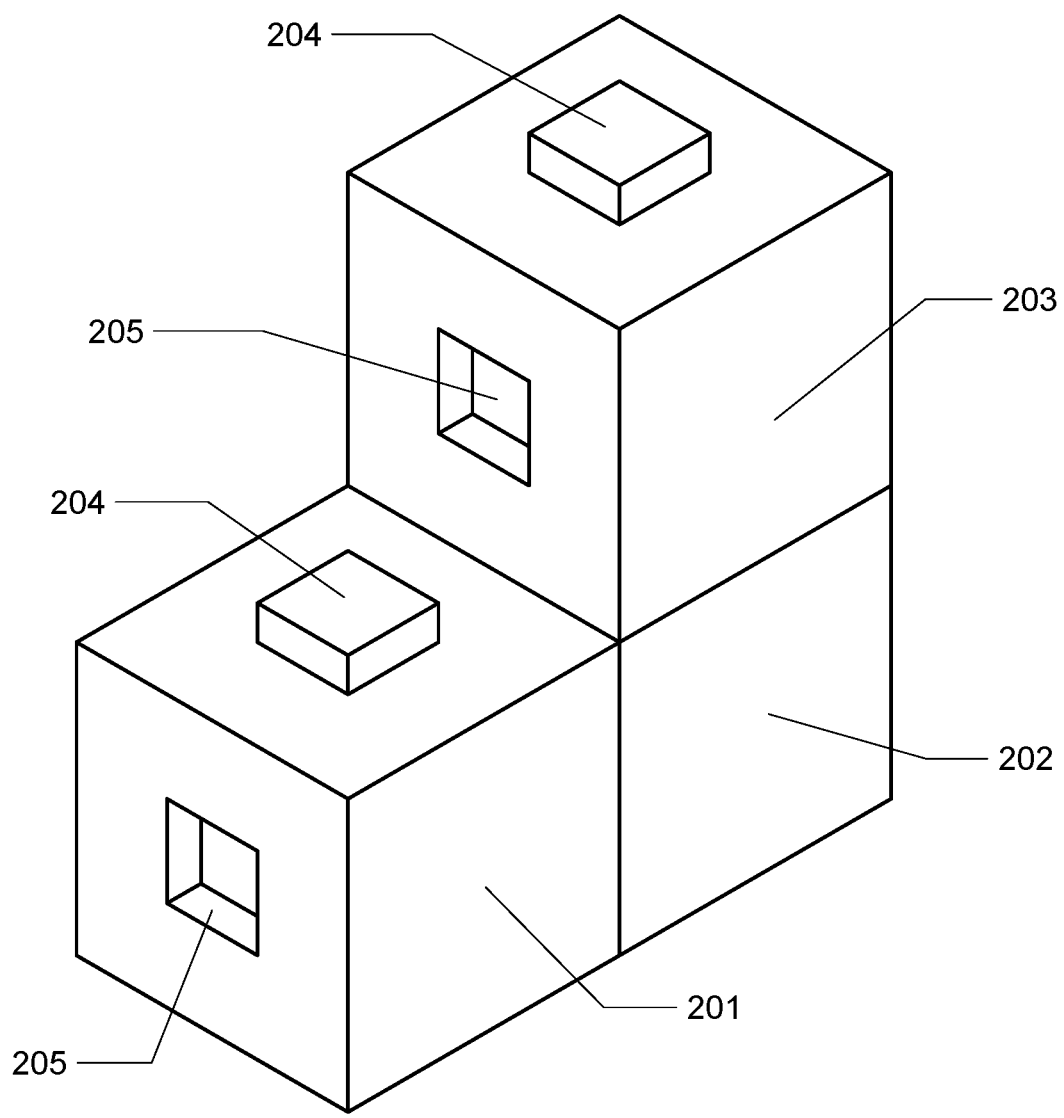
FIG. 2 depicts an exemplary continuous formation formed by three interlocking blocks (201, 202, and 203). Each block has one or more projections (204) that can fit into complementary cavities (205) on like blocks.
Figure 3:
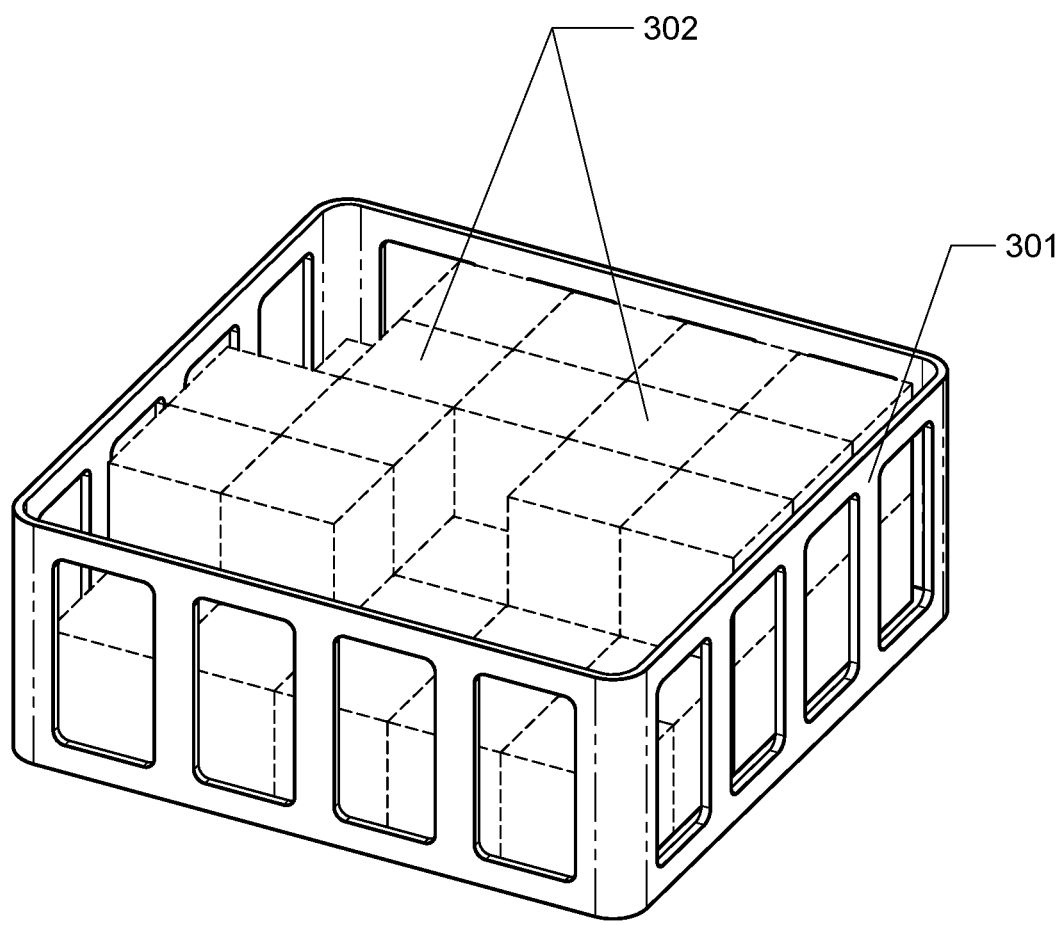
FIG. 3 depicts an exemplary implantable body comprising a continuous formation comprising multiple discreet bodies 302 of porous matrix material held in a template 301 comprising a frame or stencil.

In one implementation, the building blocks comprise interlocking components, i.e. complementary protrusions and indentations, or other complementary components, which enable two or more blocks, bricks, beams, plates, etc. to be fit together in a desired configuration. In one embodiment, the implant bodies comprise bricks similar to LEGO™ bricks, with one or more protruding elements that can fit a complementary receiving element in another brick. Exemplary interlocking blocks are depicted in FIG. 2, wherein cubic implant body blocks comprising matrix material are depicted having complemenetary protrusions and indentations. For example, in one embodiment, the invention comprises a substantially cubic block of matrix material having 1-3 protrusions and 1-3 indentations, wherein each of the protrusions and indentations are present on different faces of the cube. Implant bodies comprising multiple building blocks can be assembled prior to cell loading and implant, or may be assembled in situ, as described below.

In one embodiment, the invention comprises a kit comprising two or more implant body building blocks provided together in suitable (e.g. sterile) packaging material.

Loading of Cells into Implant Bodies. In the methods of the invention, the implant bodies are loaded with bone precursor cells prior to their implantation into the patient. Implant bodies may be loaded by pipetting the cell suspension solution onto the implant body, submerging the implant body in cell suspension, or otherwise contacting the implant body with cellular suspension for a time sufficient for the cell solution to perfuse the porous matrix material and enable the matrix material to absorb, adsorb, bind, or otherwise retain the bone precursor cells, for example a period of 30 to 75 minutes, for example 60 minutes.

In loading implant bodies with cells, an important consideration is the density of cells within the transplant matrix. The inventors of the present disclosure have advantageously derived the critical density of cells for surgically implanted material that will achieve optimal growth. In general, a concentration of 10,000 to 80,000 cells per $mm^3$ of matrix may be used, for example in the range of 20,000 to 40,000 cells per $mm^3$. Cell concentrations in densities in that exceed the critical range tend to suffer cell death from lack of sufficient nutrients and cells transplanted at densities below this critical range will often not reach sufficient critical mass to form robust bone tissue. For example, in an implant body comprising collagen sponge material, a concentration of 20,000 to 40,000 cells per $mm^3$ may be used. For example, for a collagen sponge body having a volume of 63 $mm^3$, a cell number of between 1.5 and 2.5 million cells will provide optimal performance.

Pre-Implantation Incubation. The inventors of the present disclosure have advantageously determined that the efficacy of the process of the invention is greatly improved by performing an incubation step prior to transplant. The cell suspension-soaked implant bodies may incubated at or near 37° C. for a period of 45-75 minutes. This critical incubation step allows the cells held within the matrix to adhere, adsorb, or otherwise be held by the matrix material. This adherence/binding greatly aids in the retention and organized growth of cells within the transplant matrix. After the incubation period, the implant bodies are ready for surgical implantation.

Seeded Implants. In an alternative strategy, the implant body will comprise what will be referred to as a "seeded matrix." The seeded matrix comprises a matrix material admixed with macerated bone. In the seeded matrix, the macerated bone particles provide a source of BMSC's and bone precursor cells that can propagate and populate the surrounding matrix material, eventually maturing into a bone structure that conforms to the shape of the implant Seeded matrices may be formed by admixing matrix material and macerated bone and then forming (e.g. by molding) the admixture into an implant body of the desired shape (e.g. a cube, interlocking block, or custom implant shape). For example, the admixture can be injected into a template such as an ABS template, to create a desired shape. The source of bone may be autologous (e.g. from local bone such as spinous processes, lamina, osteophytes, or the sites such as the iliac crest or femoral canal) or heterologous (e.g. from a donor or cadaver). The bone can be macerated or morselized by any mechanical means, including by mortar and pestle, grinders, blades, and other mechanical means. The particle size of the macerated bone may vary, for example, with particles of 0.25-2 mm in average diameter being used or being present as a paste. The proportion of bone to matrix material in the admixture may vary, for example, with the bone component comprising 40-80% of the mixture. In general, if the bone utilized has relatively more cancellous bone (which contains a higher proportion of BMSC's), less bone is needed. The admixture may further comprise a binding agent, such as sodium hyaluronate, glycerin, or cellulose gum, to assist the composition in holding its shape. The bone may be ground or macerated prior to admixture with the matrix material, or the two components (and any additional components, such as ascorbic acid or binding agent) can be mixed as the bone is ground.

The use of a seeded matrix provides various advantages. First, this strategy avoids the need to culture bone precursor cells and minimizes the risk of losing cells from the implant during surgery. In one implementation, the use of a seeded matrix enables a point-of-care system for creating new bone structures in a patient, comprising the following steps: bone is harvested from the patient; the bone is macerated and admixed with the porous matrix material to make a seeded matrix; the seeded matrix is formed into one or more implant bodies; and the one or more implant bodies are implanted in the patient. Such a method advantageously allows for the formation and implantation of an implant using autologous bone in a single procedure.

The seeded matrix may be functionalized with ascorbic acid at various stages. In one embodiment, the matrix material is temporarily suffused with a solution of ascorbic acid prior to its admixture with macerated bone. In another embodiment, ascorbic acid, or an ascorbic acid extended release formulation, is also admixed with the matrix material and bone when these components are combined. In another embodiment, the seeded implant body is formed, and then is subsequently exposed to a solution of ascorbic acid to functionalize it. In one implementation, the implant bodies of the invention comprise a hybrid material which has bone chips, cell-free matrix material, and cell-containing matrix material, for example in a 1:1:1 ratio.

Surgical Implantation of Implant bodies.

The scope of the invention also comprises methods of using the implant bodies, as described below. In one embodiment, the invention comprises the implantation of one or more implant bodies into the patient. In one embodiment, the invention comprises a method of forming a bone structure in a patient by implanting one or more cell-loaded implant bodies therein.

After preparation, as described above, the implant bodies are surgically introduced into the transplant site of the patient. The placement of such implant bodies may be accomplished using known methods of bone graft surgery or bone substitute implantation. If a single implant is to be used, it can be placed into position as needed. If "building block" implant bodies are used, these can be arranged in what will be referred to as a "continuous formation." As used herein, a continuous formation is a single implant body or is a plurality of multiple implant bodies configured such that each one contacts one or more adjoining blocks. It is important that the building blocks be in contact with one another to form continuous bone structures.

The continuous formation may be arranged in the patient by a surgeon or other practitioner. Alternatively, the continuous formation may be attained using the assistance of a template, for example a stencil or frame which will hold the blocks in position. In one embodiment, the template comprises a resorbable material and the template is left in the patient with the implant bodies it holds. Exemplary resorbable materials for the template include calcium hydroxylapetite and calcium phosphate apatitic calcium phosphate bone substitute (ABS), PGA, PLA, PDS, milled/machined allograft bone, woven demineralized bone fibers, and absorbable metals such as magnesium alloy. Non resorbable materials may include, for example, PEEK, titanium, and carbon fiber.

Typically, the bone structure to be formed needs to be continuous with a native bone structure within the patient's body. The bone structure formed by an implant body may be made continuous with native bone by placing at least one surface of the implant body in contact with the surface of extant bone which has been decorticated, lightly mechanically scored or otherwise treated to promote a healing response which aids in the integration of the implanted bone substitute. Alternatively, a biocompatible adhesive or a fastener (e.g. screw or anchor) can be used to secure the implant body in contact with native bone.

The implanted bodies will develop into structured bone tissue over a period of weeks to months. Portions of the matrix material may be broken down and resorbed into the body of the patient. The resulting bony structure will conform to the shape of the implant or configured implants and will not overgrow, as is common with BMP-treated implanted scaffolds. The resulting bony structure will typically have continuous marrow, normal vascularization, and a high degree of structure and organization, like native bone. Furthermore, the resulting structure will typically be fully structurally and functionally integrated with the host bone requiring repair or fusion.

Exemplary implementations of the invention are described in the following Examples.

Example 1. Protocol for Bone Substitute Preparation

Step 1. Osteoblast cell culture from bone marrow. Bone marrow was recovered using standard methods. A suspensions comprising 1:1 volume ratios of bone marrow and media was prepared. The primary media comprised: 500 mL DMEM:F12 (1:1); 50 mL FBS; and 5.5 mL antibiotic-antimycotic. The marrow was suspended in primary media in a 0.5 mL Eppendorf tube and lightly agitated to make a cell suspension. The cells were counted and a suspension containing 20 million cells in 10 mL was created. The cells were evenly distributed on a 10 cm dish and placed in an incubator at 37° C., 5% $CO_2$.

On the third day after plating, the primary media was changed to a differentiation media comprising: 50 mL primary media; 150 µL 1M β-glycerophosphate (final concentration 3 mM); and 25 µL 100 mg/mL ascorbic acid (final concentration 50 µg/mL). Media was changed every 2-3 days, with freshly prepared differentiation media used each time.

Step 2. Implant body Preparation and Cell Loading. On day 10 after plating cells from bone marrow, the cells were ready to be implanted. A pre-soak process was performed as follows. GELFOAM™ collagen sponge was cut into blocks of 3×3×7 mm. The sponge blocks were incubated in differentiation media at 37 degrees C. for 30 minutes. After 30 minutes, sterile filter paper was used to remove excess media from the sponge.

Cell recovery was performed as follows. First, 6 mL of warm 0.05% trypsin-EDTA solution was added to the 10 cm dish containing the cells and incubated at 37 degrees C. for 10-15 min. Next, a cell scraper was used to detach adherent cells and the cells were transferred to new conical tubes. 3 mL of differentiation media was added to neutralize the trypsin. The conical tube was centrifuged at 1500 rpm for 5 min to pellet the cells. The supernatant containing trypsin was aspirated and the cell pellets were resuspended in about 5 mL differentiation media.

The cycle of centrifugation, removal of the supernatant, and replacement with differentiation medium was performed to wash and remove the trypsin. This cycle may be repeated until the trypsin has sufficiently been removed, for example, 2-3 times.

For loading cells into the sponge blocks, each 63 $mm^3$ sponge was loaded with 2 million cells. This was done by pipetting the cell suspension onto the sponge. Some excess suspension was not absorbed by the sponge. The sponges were then incubated at 37 degrees C. for 1 hour. At the end of incubation, the bone implant body was complete and ready for surgical implantation.

Example 2. Creating Organized Bone Structures in Mice

Femur and tibia bones were harvested from male C57BL/6J mice. Whole bone marrow was extracted from the diaphyses of the femur and tibia bones through centrifugation. The BSMCs were allowed to grow to sufficient quantity for 3 days. After 3 days, BMSCs were transitioned to an environment with ascorbic acid enriched differentiation media. After 10 days in culture, the cells were loaded onto collagen sponges. Collagen sponges can have different shapes and sizes. In this example, four shapes were used: a small block (3×3×7 mm), a beam (3×3×20 mm), a cuboid (6×6×7 mm), and a block in the shape of the letter "T" (10×10 mm).

Cell-seeded collagen sponges were implanted subcutaneously on the back in male C57BL/6J mice. Up to 4 sponges were implanted per mouse. MicroCT was performed at 4 and 8 weeks postoperative in vivo, and at 12 weeks postoperative ex vivo.

Shape and dimensions of engineered bone followed original scaffold geometry. Implanted scaffolds self-organized into well-formed bone with cortex and marrow and maintained shape to 12 weeks post operative.

Example 3. Creating Organized Bone Structures in Mice with Multiple Matrix Material (Collagen and ABS Plastic)

Cells were prepared using the method described in Examples 1 and 2. After 10 days in culture, the cells were loaded onto collagen sponges. In this example, a dozen small blocks (3×3×7 mm) were used. A template comprising a stencil of a stylized eagle was fabricated in ABS using an additive manufacturing machine. The stencil was sterilized by submerging it in ethanol overnight.

Cell-seeded collagen sponges were placed into the template. In doing so, the sponges may deformed slightly. The implant body consisting of the cell-loaded collagen sponges surrounded by the fabricated template was implanted subcutaneously in the back of a male C57BL/6J mice. MicroCT was performed at 4 and 8 weeks postoperative in vivo. Shape and dimensions of engineered bone closely reproduced the shape defined by the template. Implanted scaffolds self-organized into well-formed bone with cortex and marrow.

Example 4. Creating Bone Structures that Integrate with Host Bone in Mice

Cells were prepared using the method described in Examples 1 and 2. After 10 days in culture, the cells were loaded onto collagen sponges. In this example, small blocks (3×3×7 mm) were used. A midline approach to the lumbar spine was performed in a C57BL/6J mice. A scalpel was used to decorticate the spinous process and lamina of the vertebral body. Ex-vivo micro CT was performed at 0, 1, 2, and 4 weeks. Minimal heterotopic ossification was seen and by 4 weeks, the newly formed bone had fully integrated with the host bone.

Example 5. Performing Multi-Level Lumbar Fusion in Mice

Cells were prepared using the method described in Examples 1 and 2. After 10 days in culture, the cells were loaded onto collagen sponges. In this example, two scaffold geometries were used: six small blocks (3×3×7 mm) and one beam (3×3×20 mm) Each animal received only one scaffold geometry.

A midline approach to the lumbar spine was performed in a C57BL/6J mice. A scalpel was used to decorticate the spinous process and lamina of the vertebral body. The sponges were placed along the dorsum of the lamina and sutured to the spinous process. Ex-vivo micro CT was performed at 8 weeks. Robust spinal fusion was seen with both scaffold geometries. Quantitative analysis indicated that the fusion bone was indistinguishable from native bone.

The results demonstrate the use of a cell-based bone graft substitute that can: self-organize within 4 weeks to form a normally structured bone, fully integrated with host bone; maintain a stable size and shape; be scaled through the use of a single, large matrix material or combination of multiple, smaller implant bodies; and be compatible with mixed matrix materials.

All patents, patent applications, and publications cited in this specification are herein incorporated by reference in their entirety to the same extent as if each independent patent, patent application, or publication was specifically and individually indicated to be incorporated by reference. The disclosed embodiments are presented for purposes of illustration and not limitation. While the invention has been described with reference to the described embodiments thereof, it will be appreciated by those of skill in the art that modifications can be made to the structure and elements of the invention without departing from the spirit and scope of the invention as a whole.

What is claimed is:

1. An implantable body for forming a bone structure within a patient, comprising
   a body comprising a porous matrix, wherein the porous matrix material is functionalized with ascorbic acid;
   wherein the porous matrix has been infused with a solution of bone precursor cells at a density between 10,000 and 80,000 cells per cubic millimeter of matrix material;
   wherein the body comprises a continuous formation comprising one or more discreet bodies of porous matrix material held in a template; and
   wherein the template comprises ABS.

* * * * *